United States Patent [19]

Seldin

[11] 4,171,570
[45] Oct. 23, 1979

[54] METHOD AND APPARATUS FOR EVALUATING ANOMALIES OF FACIAL BILATERAL SYMMETRY

[75] Inventor: Edward B. Seldin, Boston, Mass.

[73] Assignee: The Massachusetts General Hospital, Boston, Mass.

[21] Appl. No.: 845,934

[22] Filed: Oct. 27, 1977

[51] Int. Cl.² ............................................. A61C 11/00
[52] U.S. Cl. .......................................... 32/20; 32/32
[58] Field of Search ................................. 32/32, 20, 21; 33/174 D

[56] References Cited

U.S. PATENT DOCUMENTS

| | | | |
|---|---|---|---|
| 1,362,602 | 12/1920 | Coble | 32/32 |
| 1,598,535 | 8/1926 | Lentz | 32/32 |
| 1,639,626 | 8/1927 | Badger | 32/32 |
| 2,016,103 | 10/1935 | Chott | 32/32 |
| 2,219,559 | 10/1940 | Lentz | 32/32 |
| 2,545,249 | 3/1951 | Ackerman | 32/32 |
| 2,768,442 | 10/1956 | DeFurio | 32/32 |
| 2,884,696 | 5/1959 | Bonfanti | 32/32 |
| 3,510,947 | 5/1970 | Tuccillo et al. | 32/32 |

Primary Examiner—Louis G. Mancene
Assistant Examiner—John J. Wilson
Attorney, Agent, or Firm—Richard J. Birch

[57] ABSTRACT

A method and apparatus for preoperative, horizontal plane evaluation of cases with anomalies of facial bilateral symmetry are disclosed. The required rotational and translational movements in the horizontal plane are obtained by means of a graphical technique in which the coordinate system data is derived from an articulated mandibular model.

13 Claims, 13 Drawing Figures

METHOD AND APPARATUS FOR EVALUATING ANOMALIES OF FACIAL BILATERAL SYMMETRY

CROSS-REFERENCE TO RELATED APPLICATION

The present application is related to my co-pending application for Dental Surveyor and Method Therefor filed Oct. 27, 1977 as Ser. No. 846,202.

BACKGROUND OF THE INVENTION

This invention relates to preoperative evaluation techniques and more particularly to a method and apparatus for analyzing the rotational and translational movements in the horizontal plane that are required to correct an anomaly of facial bilateral symmetry.

The majority of orthognathic cases that come to surgery involve deformities predominantly in the sagittal plane. Some of these may also have minor midline discrepancies (with or without a crossbite) based on irregularities in the symmetry of one or both dental arches at the dentoalveolar level. However, cases in which the dominant feature is an anomaly of bilateral symmetry in one or both jaws at the skeletal level are relatively rare.

Cases with major or minor discrepancies in the horizontal plane as an isolated phenomenon, or in association with one of the more usual sagittal discrepancies tend to be the most challenging to evaluate preoperatively, even though they may ultimately be treated in a routine surgical manner.

Various types of work-up techniques are available to the surgeon for different kinds of deformities. Certain techniques are better than others in terms of the corrective movements that they best measure. The lateral cephalometric X-ray averages facial anatomy in the mid-sagittal plane and thus documents with great clarity the vertical and anteroposterior aspects of facial anatomy. However, because this technique averages the two sides it is practically useless in evaluating symmetry. Dental models, although confined to dentoalveolar structures, nonetheless accurately document the anatomy they record in all three dimensions. Such models are particularly usefull in revealing anomalies of bilateral symmetry. They can also be used to document both vertical and anteroposterior corrective movements in specific sagittal planes and to show vertical and lateral movements in a frontal plane.

What is lacking at the present time is a simple, effective method and apparatus for analyzing corrective movements in the horizontal plane. Unfortunately, this is exactly the plane in which one would want to measure disturbances in facial bilateral symmetry.

It is accordingly a general object of the present invention to provide a method and apparatus for analyzing the required rotational and translational movements in the horizontal plane.

It is a specific object of the invention to provide a method and apparatus for generating a graphical representation of jaw movements in the horizontal plane.

It is another object of the invention to provide a method and apparatus that utilizes the three dimensional information contained in a dental model.

It is still another object of the invention to provide an apparatus that produces an accurate and reproducable positioning of an articulated mandibular model at two unique positions.

It is a feature of the invention that the positioning of the articulated mandibular model is accomplished without reference to scalar measurements.

It is another feature of the invention that the method thereof can be implemented with relatively simple and inexpensive hardware without sacrificing the requisite degree of measurement accuracy.

BRIEF DESCRIPTION OF THE INVENTION

Dental models are made of the patient's upper and lower jaws. The maxilla model is mounted on the upper portion of a single hinge axis articulator. Two locking templates that can be removably mounted on the base of the articulator and positionally referenced thereto are prepared using the mandibular model as a male casting element. The mandibular model is mounted on the articulator first in a position corresponding to the malocclusion and a cast is then made of the base of the model. The resulting female cast of the model base includes means for positionally referencing the cast to the base of the articulator. The cast can then be used as a template to accurately locate and lock the mandibular model at the position representing the malocclusion.

The same casting technique is employed to produce a template that locates and locks the mandibular model at the position representing the proposed corrected occlusion. By using the two locking templates on the articulator, the surgeon can accurately and repeatedly locate the mandibular model at both the malocclusion and corrected occlusion positions without reference to any scalar measurements.

The mandibular model is mounted on the articular using the first or corrective locking template. Two orthogonal reference lines are then established in a horizontal plane with respect to the mandibular model with one line running transversely through any reasonable bilateral dental landmark and the other reference line being constructed at right angles to the first as the median bisector of the line segment connecting the selected landmarks. The reference "lines" can comprise lines drawn on a transparent sheet material having a cut-out that corresponds in size and shape to the female cast of the mandibular model base. In this case, the sheet is fitted over the model before the reference lines are drawn on the sheet. Alternatively, physical pointers can be attached to the model.

After establishing the reference "lines" with respect to the mandibular model in the proposed correction of occlusion position, a graph ring having an X–Y graph on the surface thereof is placed over the articulator so that the ring surrounds the anticulated mandibular model with the graph surface of the ring located in substantially the same horizontal plane as the reference "lines". The X and Y lines on the graph are numbered outwardly from the center of the ring.

The graph ring is then rotated to bring the mandibular model reference "lines" into register with the O, O X–Y coordinates of the graph. At this point without moving the graph ring, the mandibular model and locking template are removed from the articular together with the transparent reference line sheet if one was employed. The second locking template which presents the malocclusion position of the mandibular model is then mounted on the articulator. After locking the base of the mandibular model in the template, the transparent reference "lines" is fitted over the model. The reference "lines" now register a deflection with respect to the graph on the ring.

Using a separate sheet to graph paper having the same scale as the ring graph, an orgin is designated at a convenient point on the sheet and X-Y coordinates are drawn through this point in register with the graph papers. These coordinates are drawn in a first color e.g. black and are taken to represent the orientation of the patient's proposed "normal" or corrected anatomy.

The deflection of the reference "lines" as measured on the graph ring, is now transferred to the sheet of graph paper, and drawn in a second color e.g. red. These coordinates are taken to represent the deviation from "normal" to be corrected by the proposed surgery. The transferred deflection can be represented by two measurements, one of the X-Y translational coordinates of the red origin with respect to the black origin and the other of the degree of rotation of the red coordinate system about its origin with respect to the black coordinate system.

If the transparent sheet was employed, it is now removed from the model and its reference lines superimposed on the red and black coordinates on the graph paper. In each position the base of the model is traced onto the graph paper in appropriate colors. If the physical "lines" or pointers were used, then the model itself together with the pointers is placed on the graph paper and the pointers are aligned with respect to each coordinate system. The base configuration of the model can then be drawn on the graph paper in each position in the appropriate color.

The motion in the horizontal plane of any point of interest in the mandible can be demonstrated by marking the corresponding point on the transparent sheet and then moving the sheet from one set of coordinates to the other. The point of interest (e.g., condylar head, angle of mandible, etc.) is transferred from the sheet to the graph paper in appropriate colors to match coordinate systems.

Having briefly discussed the method and general apparatus of my invention, I will now describe in detail a preferred embodiment of my invention, selected for purposes of illustration and shown in the accompanying drawings, in which;

FIG. 12 is a view in perspective of an alternative embodiment of the coordinate locator that utilizes at least one spring-loaded pincer and orthogonal pointers; and, FIG. 13 is a view in side elevation of the coordinate locator embodiment shown in FIG. 12.

A DETAILED DESCRIPTION OF A PREFERRED EMBODIMENT

Turning now to the drawings and in particular to FIGS. 1-4 thereof, there is shown a dental articulator indicated generally by the reference numeral 10, that is removably mounted on a mounting plate 12. The articulator 10 comprises: an articulator base 14 having a locating pin 16 and a locating dimple 18; a pair of wire pivot frame arms 20a-20b and 22a-22b which define circular bearings 20c and 22c, respectively; a pivot rod 24 that is removably positioned within bearings 20c and 22c; and a dental cast holder 26 that is rotatably mounted with respect to pivot rod 24 by means of cantilever pivot arms 28 and 30 which terminates in corresponding bearings 28a and 30a through which extends the previously mentioned pivot rod 24.

Figure 1:
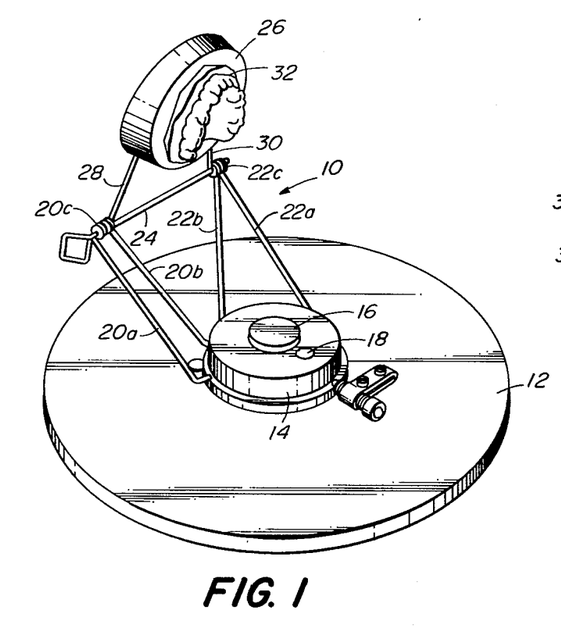
FIG. 1 is a view in perspective showing an articulator mounted on a base plate.
Figure 2:
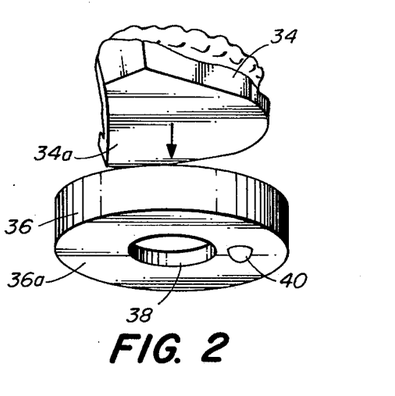
FIG. 2 is a view in perspective from below of a mandibular model and a locking template.
Figure 3:
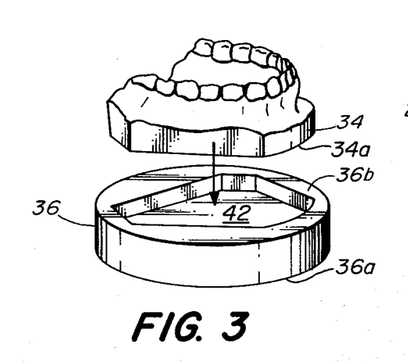
FIG. 3 is a view in perspective from above showing the locking fit of the FIG. 2 mandibular model within the locking template.
Figure 4:
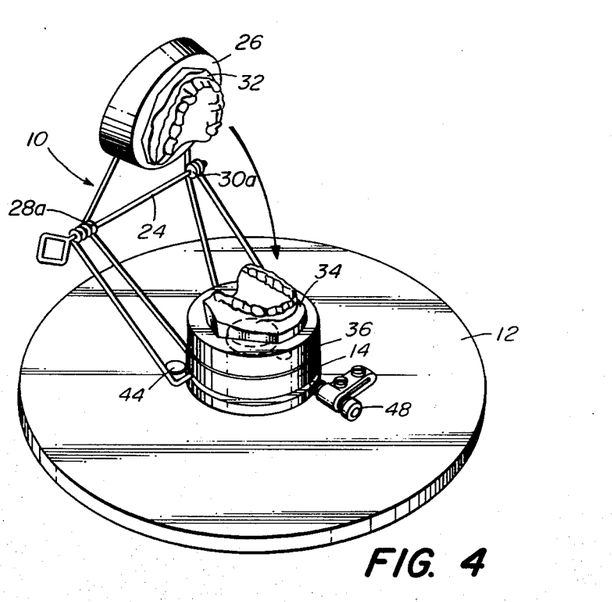
FIG. 4 is a view in perspective similar to that shown in FIG. 1, but with the addition of the mandibular model mounted on the articulator.

The articulator upper cast holder 26 is designed to accommodate and hold a dental model 32 of the patient's upper jaw. The articulator base 14 also is designed to accommodate and hold a model 34 of the lower jaw, but with the addition of an intermediate locking template 36 as shown in FIGS. 2-4. The locking template 36 has a central aperture 38 that corresponds in both size and shape to the upwardly extending locating pin 16 on the articulator base 14. In addition, the bottom surface 36a of the locking template is provided with a downwardly extending, hemispherical locking pin 40 that corresponds in both size and shape to the dimple 18 formed in articulator base 14. Thus, when the locking template 36 is assembled in superposed relation on the articulator base 14, as shown in FIG. 4, the locking template 36 is accurately located and positionally referenced to the articulator base 14.

Looking at FIG. 3, the upper surface 36b of the locking template has formed therein a receptacle or template 42 having the same size and configuration as the base 34a of the mandibular model 34. Therefore, when the base 34a of the mandibular model is positioned within receptacle 42, as indicated in FIG. 3 by the arrow, the mandibular model is accurately located within and positionally referenced with respect to the locking template 34 which in turn is positionally referenced to the articulator base 14.

Given this physical arrangement, it will be appreciated that the upper and lower dental models 32 and 34, respectively, are accurately positioned with respect to each other by means of the articulator positioned with respect to each other by means of the articulator which permits movement of the upper model 32 vertically around the horizontal pivot axis provided by pivot rod 24. This movement is illustrated in FIG. 4 by the arrow.

The articulator 10 is removably mounted on the mounting plate 12 by means of a 3-point mounting system comprising locator pins 44 and 46 (See FIGS. 1, 4–6, and 8–10) and a threaded locking screw 48. The 3-point arrangement provides for simple and fast mounting and dismounting of the articulator on the plate 12. Obviously, other mounting systems can be used in conjunction with plate 12 which itself is merely illustrative of a base surface for the articulator 10.

Figures 5, 6:
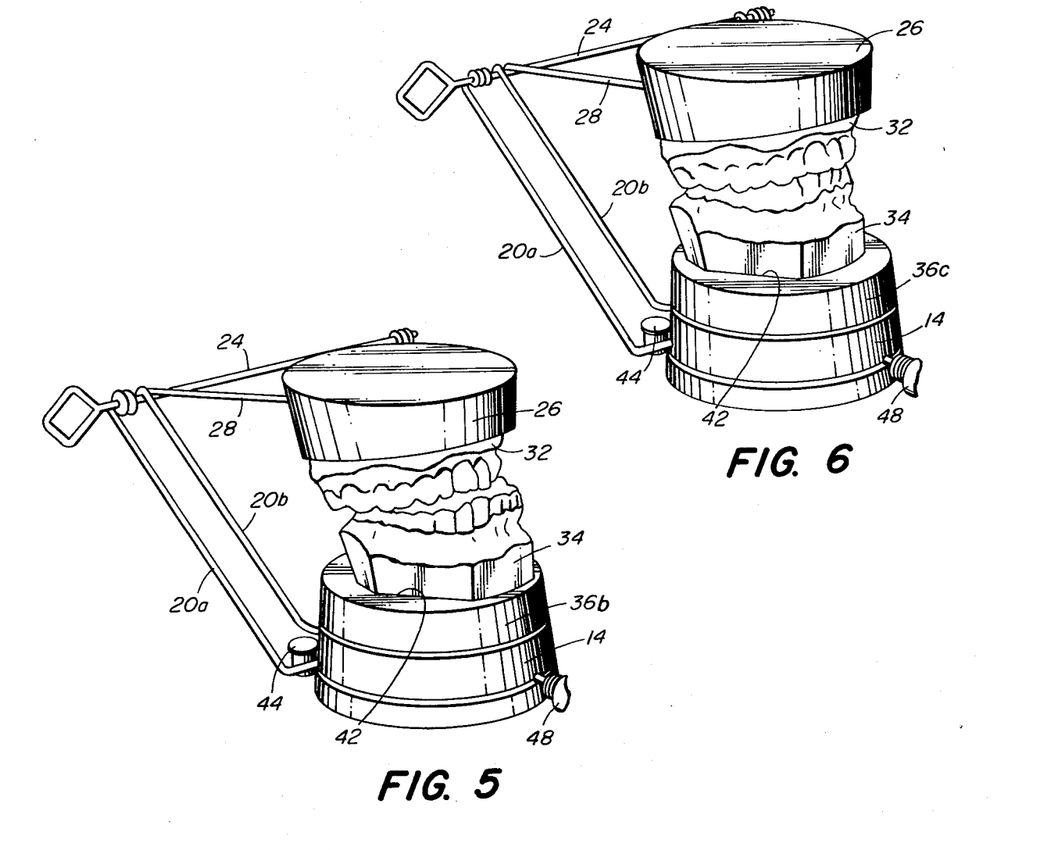
FIG. 5 is a view in perspective shows the manidulator model mounted on the articulator in the malocclusion position.
FIG. 6 is a view in perspective showing the mandibular model mounted on the articulator in the proposed corrective occlusion position.

Referring now to FIGS. 5 and 6, the mandibular model 34 is shown in the malocclusion position in FIG. 5 and in the proposed corrective or "normal" occlusion position in FIG. 6. The structural components illustrated in FIGS. 5 and 6 are identical except for the intermediate locking templates 36b and 36c which have the receptacle 42 positioned at different locations with respect to the articulator base 14.

The templates 36b and 36c are produced by conventional dental casting techniques. The mandibular model 34 is positioned as shown in FIG. 5 with respect to the upper jaw model 32 using a bite registration obtained from the patient and temporarily held in that position by suitable means (not shown). A form (not shown) is fitted around the articulator base 14 accommodating the base 34a of the mandibular model. The mold space in the form is then filled with a suitable casting material which when cured produces the template 36b. It will be appreciated that by using this technique, the template 36b accurately records the three dimensional coordinates of the mandibular model 34 in the malocclusion position.

The same technique is employed to produce the corrective template 36c. However, the mandibular model 34 is positioned in the desired corrective position with respect to the upper jaw model 32, as shown in FIG. 6 before the casting material is then placed in the mold space in the form. The pair of templates together record the translational and rotational movements embodied in corrective procedure.

Given the positional relationships of the articulator base 14, locking template 36 and the mandibular model 34, it is possible to produce two unique positions for the mandibular model that represent the corrective i.e. "normal" and the malocclusion positions. The two positions are achieved by using the appropriate intermediate locking template 36b or 36c between the articular base 14 and the mandibular model 34.

Figure 7:
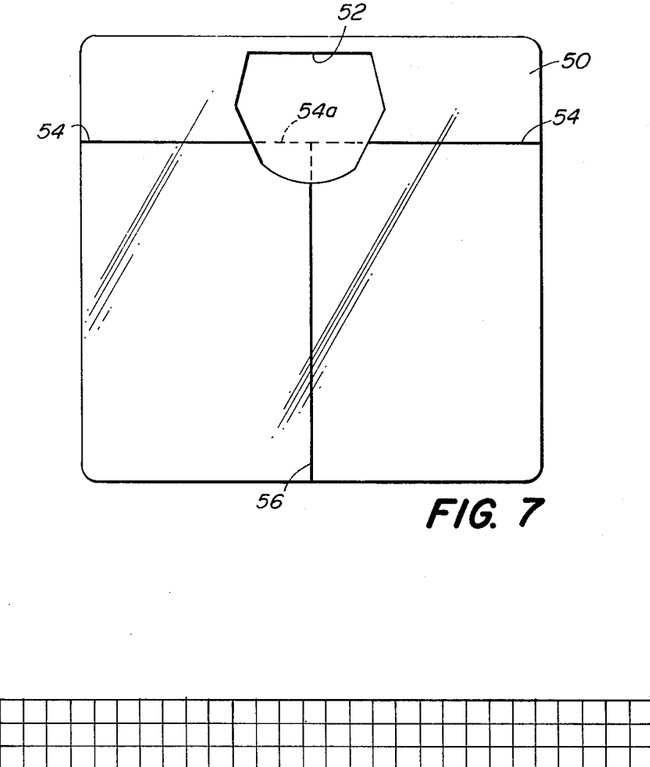
FIG. 7 is a plan view of a transparent sheet coordinate locator.
Figure 8:
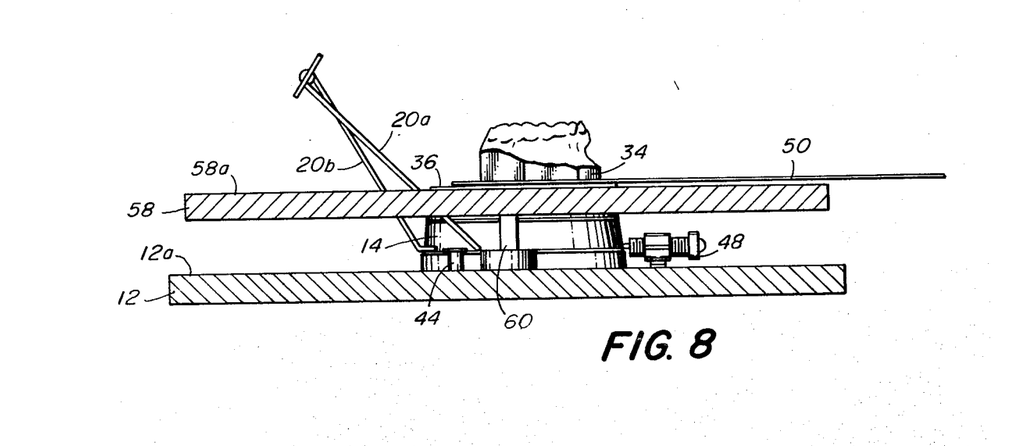
FIG. 8 is a view in side elevation and partial section showing the articulator, base plate, graph ring and the transparent coordinate locator positioned over and at the base of the mandibular base.
Figure 9:
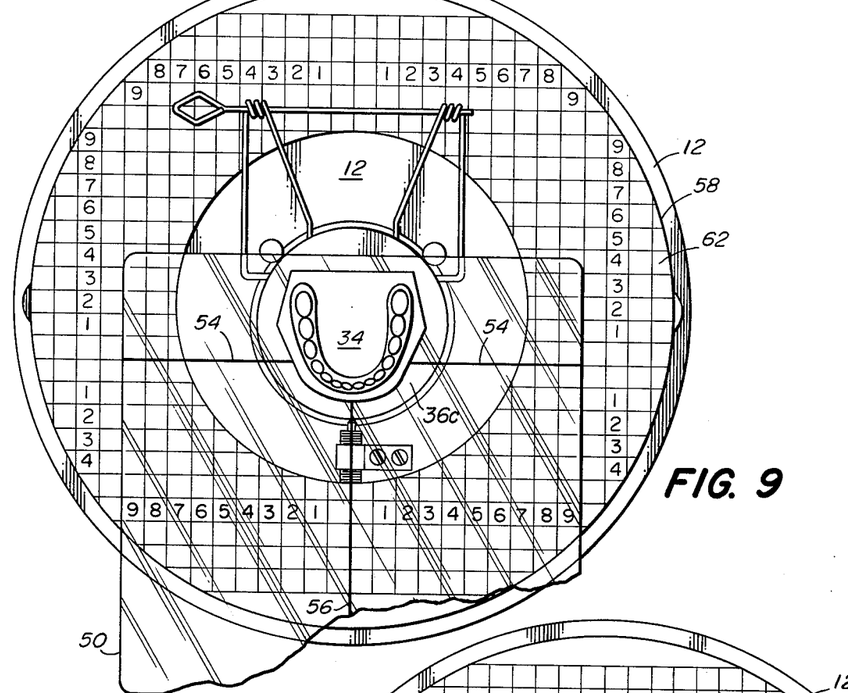
FIG. 9 is a plan view of the articulator, base plate, graph ring and coordinate locator showing the mandibular model and coordinate locator in the preposed corrective occlusion position.
Figure 10:
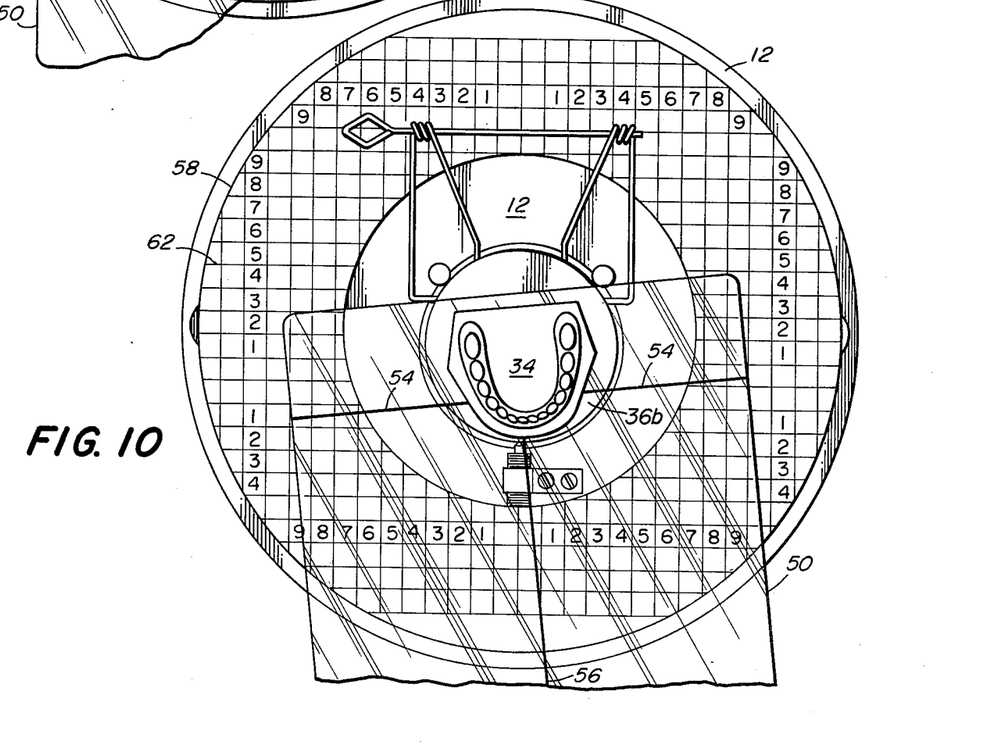
FIG. 10 is a plan view similar to that of FIG. 9, but showing the mandibulor model and coordinate locator in the malocclusion psoition.

Referring now to FIG. 7 there is shown in plan view, a coordinate locator 50 formed from a transparent sheet material, preferably plastic. The coordinate locator has a cut-out portion 52 of the same size and shape as that of the locking template receptacle 42 which was formed during the casting operation by the mandibular model base 34a. The cut-out 52 permits the coordinate locator 50 to be positioned over the mandibular model as shown in FIGS. 8–10. Two reference lines 54 and 56 are drawn on the coordinate locator with line 54 running transversely through any reasonable bilateral dental landmarks (e.g., canines, first or second bicuspids or first molars). The second reference line 56 is drawn at right angles to the first reference line as the median bisector or of the line segment connecting the selected landmarks. This line segment is indicated by the dashed line 54a in FIG. 7.

The coordinate locator 50 is used in conjunction with a graph ring 58 that is shown in side view and partial section in FIG. 8 and in plan view in FIGS. 9 and 10. The graph ring 58 has a plurality of support legs 60, one of which is shown in FIG. 8, that position the ring so that the upper surface 58a thereof is in a horizontal plane substantially the same as the horizontal plane defined by the upper surface of the locking templates 36b and 36c, as seen in FIG. 8. Preferably, the graph ring 58 is formed of a heavy metal to prevent movement of the ring during subsequent operations that will be explained below.

A graph paper 62 is glued to the upper surface 58a of the graph ring, as shown in FIGS. 9 and 10. The graph paper 62 has centimeter or outer sedar rulings with the X and Y coordinge lines numbered outwardly from the center.

Having described the structural components of the invention, it will now be helpful to discuss how those components are used in practicing the method of the invention. Assuming that the appropriate locking templates 36b and 36c shown in FIGS. 5 and 6 have been cast, the articulator 10 is mounted on the mounting plate 12 using the two locating pins 44 and 46 and the locking screw 48. The proposed corrective or "normal" locking template 36c is then positioned in superposed relation with respect to the articulator base 14 and rotated until the locating pin 42 falls into dimple 18. The graph ring 58 is now placed over the articulated mandibular model and lowered until its legs engage the upper surface 12a of the base plate 12. At this point, the base of mandibular model 34 is placed through the cut-out in transparent coordinate locator sheet 50 and positioned within the template receptacle 42. Alternatively, the mandibular model 34 can be positioned within the template receptacle 42 and the combination rotated until the locking template locator pin 40 engages dimple 18.

The graph ring 58 now is rotated until the reference lines 54 and 56 are brought into registration with the O,O X-Y coordinates of the graph paper 62 affixed to the graph ring 58. This configuration is illustrated in FIG. 9.

Taking care that the graph ring now remains undisturbed, the mandibular model is dismounted and the template 36b presenting malocclusion is substituted for the corrective or "normal" template 36c. The mandibular model is then positioned within the receptacle in template 36b. In order to accomplish this, the coordinate locator sheet 50 moves with the mandibular model to the position shown in FIG. 10. At this point, the reference lines 54 and 56 on the coordinate locator register a deflection with respect to the graph paper on graph ring 58.

Figure 11:
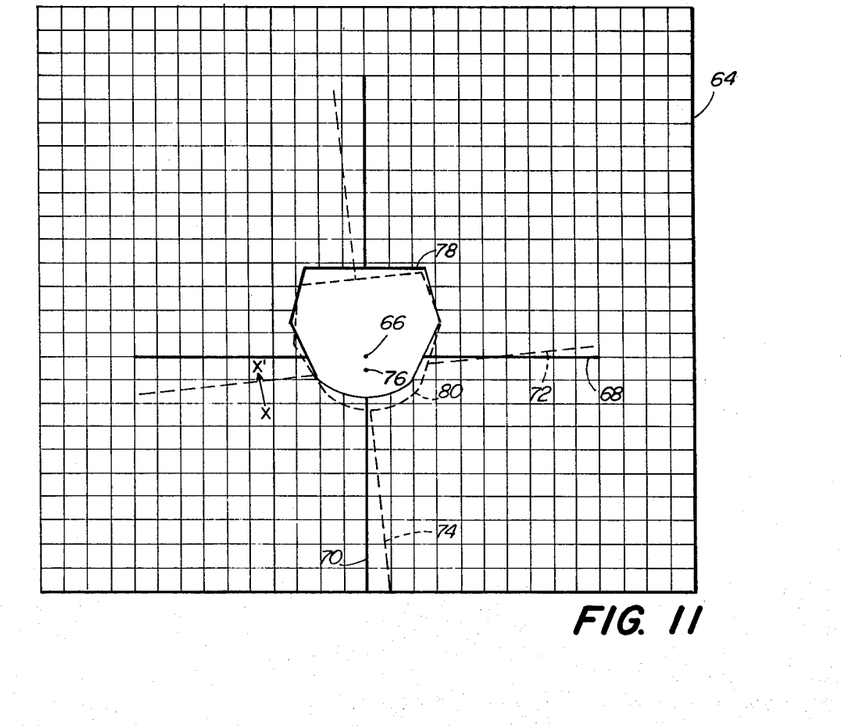
FIG. 11 is a graphical representation of the mandibular model positions shown in FIGS. 9 and 10.

Referring now to FIG. 11, there is shown a separate sheet of graph paper 64 having the same scale as the graph paper 62 used on the graph ring. An origin 66 is designated at a convenient point such as, the middle of the sheet, and the X and Y coordinates 68 and 70 are drawn through this point in register with the graph paper. These coordinates are drawn in a first color e.g. black and taken to represent the orientation of the patient's proposed "normal" or corrected anatomy.

The deflection of the lines of reference 54 and 56 from the coordinate locator 50, as measured on the graph ring, is now read on the graph ring 58 and transferred to the sheet of graph paper 64 and drawn in a second and different color e.g., red and illustrated in FIG. 11 by the dashed lines 72 and 74. This deflection represents the deviation from "normal" to be corrected by the proposed surgery.

The deflection can be represented by two measurements, one of the X-Y translational coordinates of the "red" origin 76 with respect to the "black" origin 66 and the other of the degree of rotation of the red coordinate system 72-74 about its origin with respect to the black coordinate system 68-70.

The lines of reference shown in FIG. 11 were selected for the sake of convenience to correspond to dental landmarks, but other than this they are of course arbitrary. It will be appreciated that any such lines can be used. The basic concept is that by having accurately measured the motion of any reference coordinate system that moves with the part to be surgically repositioned, one can calculate how any contiguous anatomic site of interest may be expected to move. This capability is extremely valuable in planning surgery.

The transparent coordinate locator sheet 50 is now removed from the mandibular model and its referenced lines 54 and 56 are superimposed first on the "black" coordinates 68 and 70 and then on the "red" coordinates 72 and 74. In each position the base of the mandibular model is traced onto the graph paper in appropriate colors and indicated for the "black" system by tracing 78 and for the "red" coordinates by the tracing 80.

Assuming for purposes of illustration that when one considers the surgical movement of the mandible, it will be noted that the motion in horizontal plane of any point of interest in the mandible can be demonstrated by marking the corresponding point on the transparent coordinate locator and then moving the locator from one set of coordinates to the other. This is depicted in FIG. 11 by the location of X in the "red" coordinate system which moves to point X' in the "black" coordinate system.

Figures 12, 13:
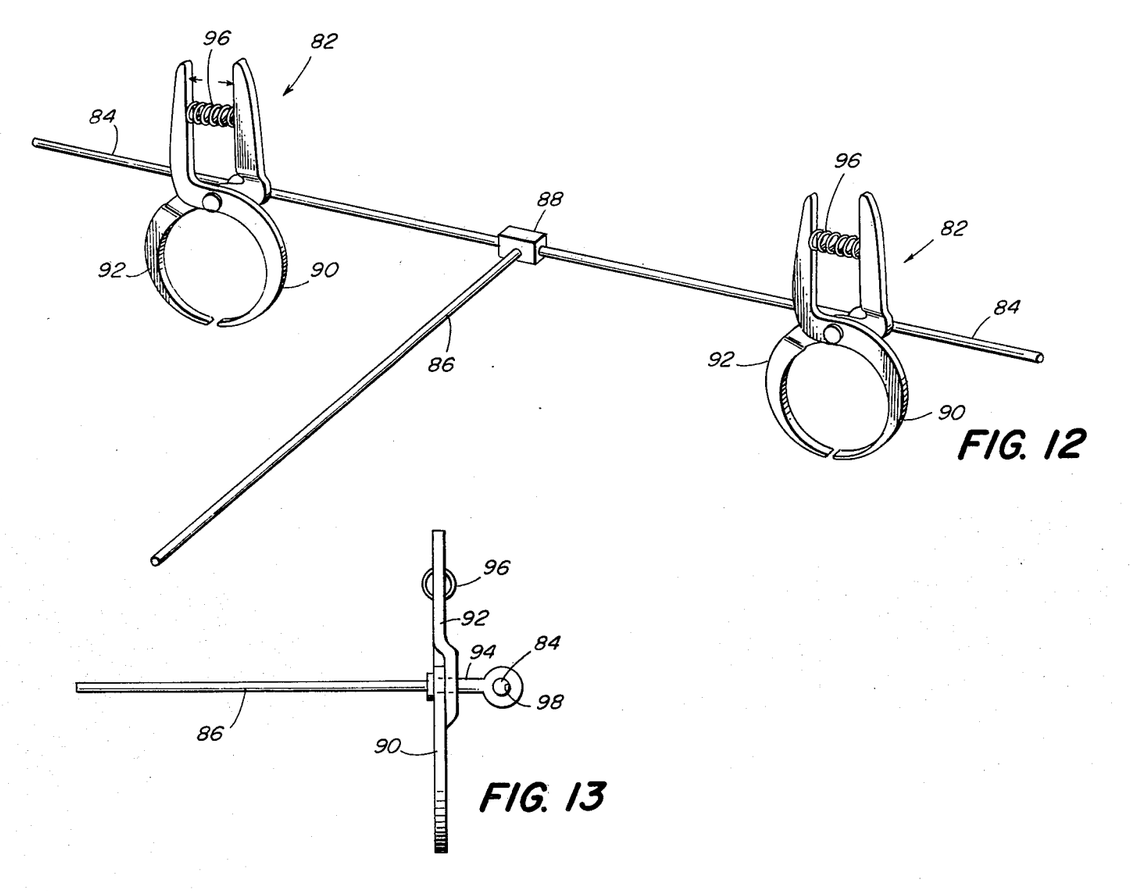

Referring now to FIGS. 12 and 13, there is shown an alternative embodiment of the reference coordinator locator 50 which utilizes a pair of spring-loaded pincers indicated, generally by the reference numeral 82. The pincers 82 are slidably mounted on pointers 84 so that the spacing between the two pincers can be adjusted to accomodate various sizes of the mandibular models. A pointer 86 is orthogonally mounted with respect to the pointers 84 by means of a mount 88. It will be appreciated that the pointers 84 and 86 correspond to the previously described reference lines 54 and 56, respectively, on the transparent coordinate locator shown in FIG. 7.

The construction of the spring-loaded pincers 82 is straightforward and conventional. Each pincer has a pair of arcuate pincer arms 90 and 92 that are pivotally secured together by pivot means 94. A compression spring 96 maintains the ends of the pincer arms 90 and 92 in abutting relation. The pincer arm pivot 94 has an aperture 98 to accomodate pointer 84. Given this configuration, it can be seen that the pincers 82 can be moved along their corresponding pointers 84 to accomodate variable spacing in the mandibular model. When the pincers are mounted on the mandibular model, the orthogonal pointers 84 and 86 function in the same manner as the previously described coordinate locator reference lines 54–56, respectively.

Having described in detail the preferred embodiment of my invention, it will now be apparent to those skilled in the art that numerous modifications can be made therein without departing from the scope of the invention as defined in the following claims. Although the invention has been described with respect to mandibular or other dental models, it should be understood that the invention is not limited to analyzing the movement of such models, but instead is applicable to determining the rotational and translational movements of other anatomic areas of interest.

What I claim and desire to secure by Letters Patent of the United States is:

1. A method for preoperative evaluation comprising the steps of:
    1. preparing maxillary and mandibular dental models, said models each having a base portion of a given configuration;
    2. mounting a articulator base on a dental articulator, said articulator base having at least one positional keying means;
    3. placing said models on the articulator in a first position that presents the patient's malocclusion and then temporarily securing the models in said first position;
    4. casting a first template means having (1) a complementary replica of the base portion of one of said dental models when the model is in such first position and (ii) at least one positional keying means that mates with said at least one positional keying means of said articulator base;
    5. unsecuring said dental models from said first position;
    6. placing said dental models on the articulator in a second position that presents the patient's proposed corrective position and then temporarily securing the models in said second position;
    7. casting a second template means having (1) a complementary replica of the base portion of said one of said dental models when the model is in said second position and (ii) at least one positional keying means that mates with said at least one positional keying means on said articulator base;
    8. unsecuring said dental models from said second position;
    9. placing the base of one of said dental models in the complementary replica thereof in one of said template means and engaging the positional keying means thereof with the positional keying means of articulator base;
    10. establishing a coordinate reference system with respect to the dental model in said one of said template means;
    11. substituting the other of said template means for said one of said template means and thereafter;
    12. determining the deviation of said dental model with respect to said established coordinate reference system; and,
    13. determining from said coordinate reference system and from the deviation therefrom the rotational and translational movements required to move said one of said models from the first position to the second position.

2. The method of claim 1 wherein said one of said dental models is the mandibular model and it is placed in said one of said template means and thereafter is placed on the other of said template means.

3. The method of claim 1 wherein said coordinate system is established by forming an orthogonal coordinate system with respect to selected points in the dental model when it is in said one of said template means.

4. The method of claim 3 wherein said deviation of the dental model is determined by obtaining the orthogonal coordinates of the dental model with respect to the coordinate system when the model is placed in said other template means.

5. The method of claim 3 wherein said coordinate system is established by placing a planar orthogonal coordinate scale around at least a portion of the dental model and placing an orthogonal reference lines forming means over at least a portion of said scale, said reference lines forming means being oriented with respect to said selected points in the dental model.

6. The method of claim 5 wherein said reference lines forming means comprises a transparent sheet having an aperture therein of the same configuration as the base portion of said one of said dental models and having orthogonal references lines formed thereon with the intersection of said lines occurring within said aperture and further comprising the the step of placing said sheet over the dental model with the sheet aperture and model base in interlocking engagement and with the reference lines overlying at least a portion of the scale.

7. The method of claim 5 wherein said reference lines forming means comprises a pair of orthogonally mounted pointers having means for removably mounting the pointers on said dental model and further comprising the step of mounting said pointers on said dental model with the pointers overlying at least a portion of the scale.

8. A method for preoperative evaluation comprising the steps of:
 1. preparing first and second three dimensional anatomical models, said models each having a base portion of a given configuration;
 2. mounting a articulator base on an articulator, said articulator base having at least one positional keying means;
 3. placing said models on the articulator in a first position and temporarily securing the models in said first position;
 4. casting a first template means having (i) a complementary replica of the base portion of one of said models when the model is in such first position and (ii) at least one positional keying means that mates with said at least one positional keying means of said articulator means;
 5. detaching said models from said first position;
 6. placing said models on the articulator in a second position and then temporarily securing the models in said second position;
 7. casting a second template means having (i) a complementary replica of the base portion of said one of said models when the model is in said second position and (ii) at least one positional keying means that mates with said at least one positional keying means on said articulator base;
 8. detaching said models from said second position;
 9. placing the base of one of said models in the complementary replica thereof in one of said template means and engaging the positional keying means thereof with the positional keying means of articulator base;
 10. establishing a coordinate reference system with respect to the model in said one of said template means;
 11. substituting the other of said template means for said one of said template means and thereafter;
 12. determining the deviation of said model with respect to said established coordinate reference system; and,
 13. determining from said coordinate reference system and from the deviation therefrom the rotational and translational movements required to move said one of said models from the first position to the second position.

9. An apparatus for preoperative evaluation comprising in combination:
 1. a dental model articulator;
 2. a planar, orthogonal coordinate scale means positioned around at least a portion of the articulator;
 3. means for forming orthogonal reference lines; and,
 4. means for removably mounting said reference lines forming means with respect to a dental model when the dental model is mounted on said articulator whereby the dental model mounted orthogonal reference lines forming means provides an indication of the position of the articulator mounted dental model with respect to said planar, orthogonal coordinate scale means.

10. The apparatus of claim 9 wherein said reference lines forming means comprises a transparent sheet means having orthogonal reference lines formed thereon.

11. The apparatus of claim 10, wherein said transparent sheet has an aperture therein which cooperatively engages the dental model when it is mounted on the dental model articulator.

12. The apparatus of claim 11 wherein said transparent sheet means has the orthogonal reference lines formed thereon with the intersection of said lines occurring within said aperture.

13. The apparatus of claim 9 wherein said reference lines forming means comprise: a pair of orthogonally mounted pointers and wherein said means for removably mounting the reference lines forming means comprise at least one spring-loaded pincer secured to one of said orthogonally mounted pointers.

* * * * *